(12) United States Patent
Arru et al.

(10) Patent No.: US 7,220,277 B2
(45) Date of Patent: May 22, 2007

(54) PROSTHESIS FOR ANNULOPLASTY COMPRISING A PERFORATED ELEMENT

(75) Inventors: Pietro Arru, Vernone (IT); Giovanni Bergamasco, Turin (IT); Carla Stacchino, Turin (IT)

(73) Assignee: Sorin Biomedica Cardio S.p.A. (IT)

( * ) Notice: Subject to any disclaimer, the term of this patent is extended or adjusted under 35 U.S.C. 154(b) by 338 days.

(21) Appl. No.: 10/393,448

(22) Filed: Mar. 20, 2003

(65) Prior Publication Data

US 2003/0220686 A1 Nov. 27, 2003

(30) Foreign Application Priority Data

Mar. 27, 2002 (EP) .................................. 02425190

(51) Int. Cl.
*A61F 2/24* (2006.01)
(52) U.S. Cl. ..................................... 623/2.36; 623/2.38
(58) Field of Classification Search ........ 623/2.36–2.4, 623/1.15
See application file for complete search history.

(56) References Cited

U.S. PATENT DOCUMENTS

| | | | |
|---|---|---|---|
| 3,656,185 A | 4/1972 | Carpentier | |
| 4,055,861 A | 11/1977 | Carpentier et al. | |
| 4,917,698 A | 4/1990 | Carpentier et al. | |
| 5,041,130 A | 8/1991 | Cosgrove et al. | |
| 5,061,277 A | 10/1991 | Carpentier et al. | |
| 5,064,431 A | 11/1991 | Gilbertson et al. | |
| 5,084,151 A | 1/1992 | Vallana et al. | |
| 5,104,407 A | 4/1992 | Lam et al. | |
| 5,133,845 A | 7/1992 | Vallana et al. | |
| 5,370,684 A | 12/1994 | Vallana et al. | |
| 5,387,247 A | 2/1995 | Vallana et al. | |
| 5,423,886 A | 6/1995 | Arru et al. | |
| 5,607,471 A | 3/1997 | Seguin et al. | |
| 5,674,279 A | 10/1997 | Wright et al. | |
| 5,716,397 A | 2/1998 | Myers | |
| 5,824,066 A | 10/1998 | Gross | |
| 5,873,812 A | 2/1999 | Ciana et al. | |
| 6,102,945 A | 8/2000 | Campbell | |
| 6,106,550 A | 8/2000 | Magovern et al. | |
| 6,143,024 A | 11/2000 | Campbell et al. | |
| 6,217,610 B1 * | 4/2001 | Carpentier et al. | 623/2.37 |
| 6,250,308 B1 | 6/2001 | Cox | |
| 6,309,414 B1 * | 10/2001 | Rolando et al. | 623/1.15 |
| 6,406,493 B1 | 6/2002 | Tu et al. | |
| 6,565,603 B2 | 5/2003 | Cox | |

(Continued)

FOREIGN PATENT DOCUMENTS

EP 0 338 994 A1 10/1989

(Continued)

OTHER PUBLICATIONS

European Search Report for EP 01830378.4 (3 pages).

(Continued)

*Primary Examiner*—Eduardo C. Robert
*Assistant Examiner*—Javier G. Blanco
(74) *Attorney, Agent, or Firm*—Faegre & Benson LLP

(57) ABSTRACT

A prosthesis for annuloplasty comprising a laminar or tubular element having a plurality of apertures along at least one portion. Preferably, the shape, dimensions, and arrangements of the apertures in this prosthesis are chosen in such a way as to give the prosthesis a differentiated flexibility in dependence on the location and direction of application of an external stress.

26 Claims, 4 Drawing Sheets

U.S. PATENT DOCUMENTS

| | | |
|---|---|---|
| 6,749,630 B2 | 6/2004 | McCarthy et al. |
| 6,797,001 B2 | 9/2004 | Mathis et al. |
| 2001/0021874 A1 | 9/2001 | Carpentier et al. |
| 2002/0010504 A1 | 1/2002 | Alt |
| 2003/0199974 A1 | 10/2003 | Lee et al. |
| 2003/0208264 A1 | 11/2003 | McCarthy et al. |

OTHER PUBLICATIONS

U.S. Appl. No. 10/164,358, filed Jun. 5, 2002 (18 pages).
European Search Report for EP 02425190.2 (3 pages).

* cited by examiner

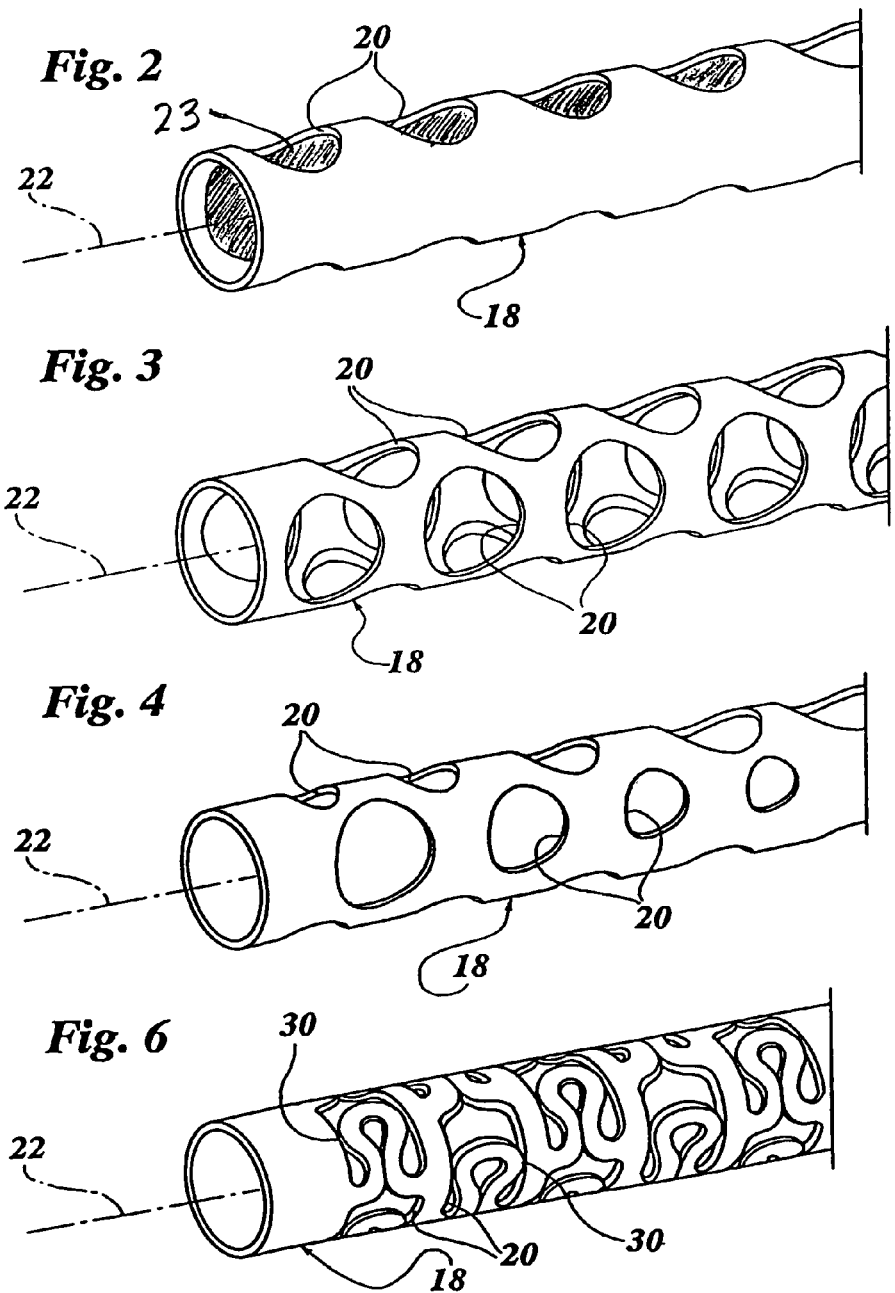

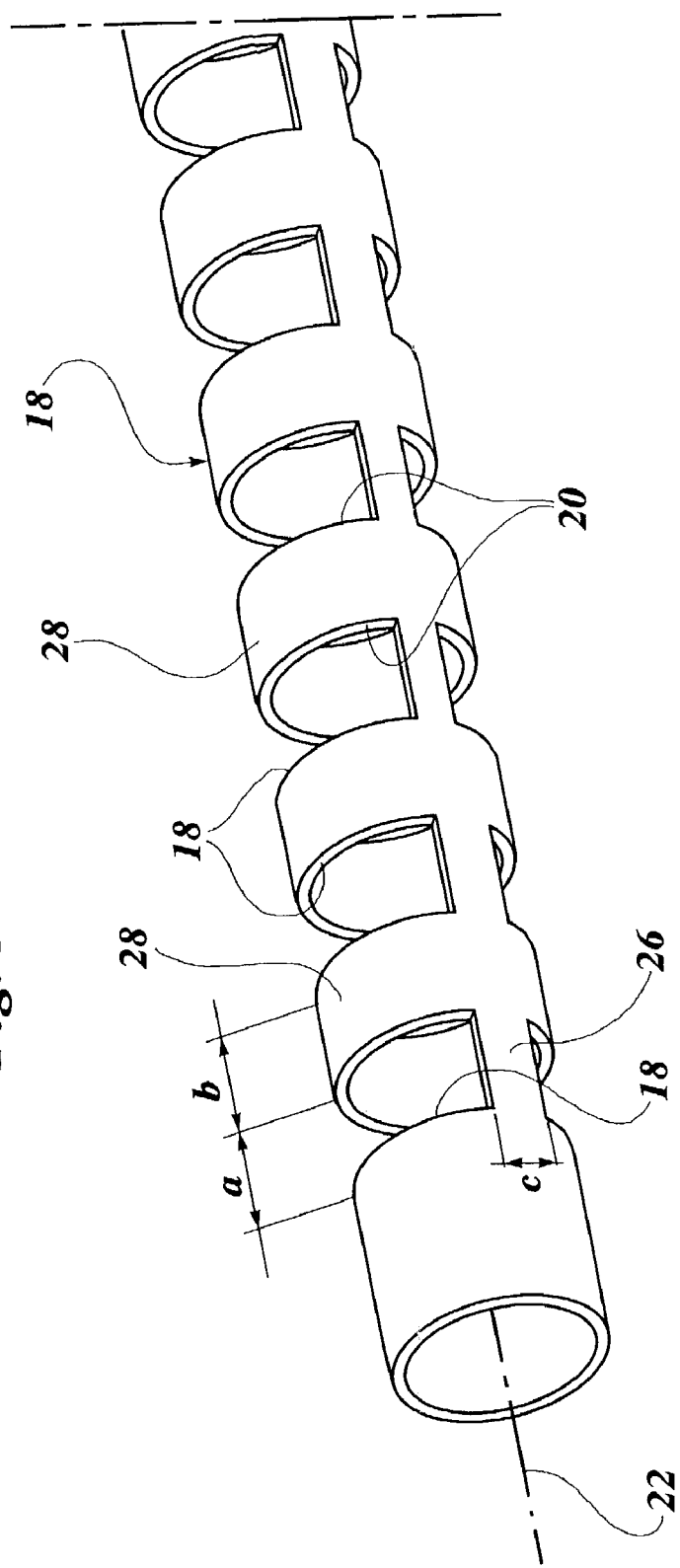

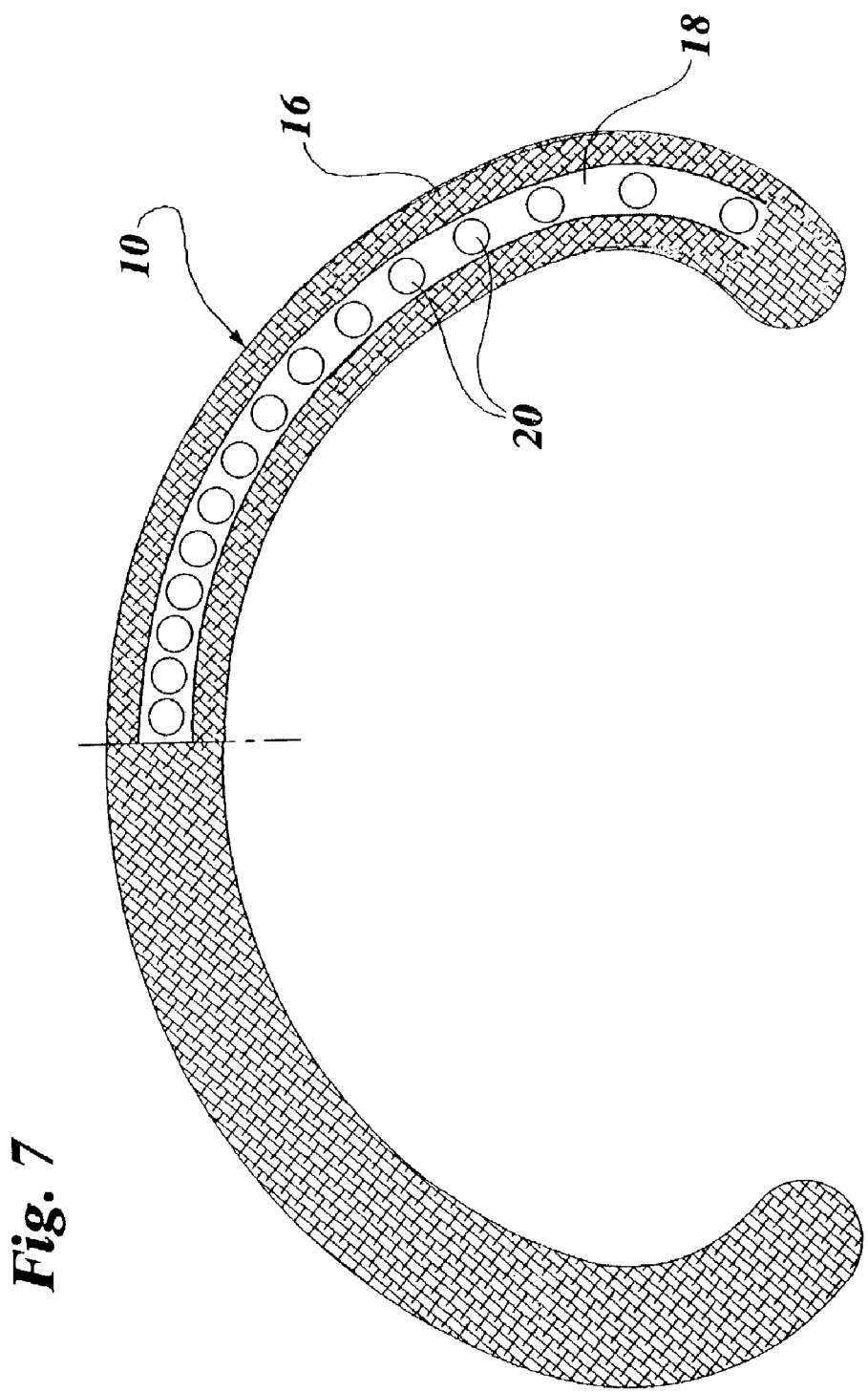

PROSTHESIS FOR ANNULOPLASTY COMPRISING A PERFORATED ELEMENT

TECHNICAL FIELD

The present invention relates in general to a device for cardiac valve repair operations and, in particular, to a prosthesis for annuloplasty.

BACKGROUND

The human heart has four cardiac valves: the mitral valve, the tricuspid valve, the pulmonary valve and the aortic valve. The mitral valve is situated in the left atrio-ventricular ostium and regulates the unidirectionality of the flow of blood from the atrium to the ventricle. It opens in the diastole and closes in the systole, preventing blood from flowing back from the ventricle to the atrium. The annulus of a normally functioning mitral valve is characterized by shape, dimensions and flexibility such as to allow a correct closure of the valve lips during the systolic phase. For example, the mitral annulus has a characteristic "kidney" shape (or "D" shape), and is more flexible in the portion corresponding to the posteria lip of the valve. Illnesses or genetic defects can cause deformations or dilatations of the annulus of the mitral valve, resulting in an incomplete closure thereof with consequent regurgitation of blood. The same phenomena can occur in the tricuspid valve, situated between the right atrium and right ventricle.

A frequently used method for eliminating some pathological alterations of the mitral and tricuspid valves is that of reinstating the correct shape and dimensions of the value annulus by means of surgical procedures known as annuloplasty. Annuloplasty comprises surgically implanting a supporting prosthesis on the dilated or deformed annulus for the purpose of reinstating its dimensions and/or physiological shape in such a way as to allow the cardiac valve to function correctly.

Support prostheses utilized in valve repair operations are called annuloplasty prostheses. In the majority of cases such prostheses are constituted by a closed or open ring structure comprising an inner core and an outer cladding of biocompatible material which allows surgical suture.

Annuloplasty prostheses of various types have been described in the prior art. Initially, the prostheses proposed were predominantly of the rigid type for the purpose of drastically reducing the dilatation of the valve annulus. Such prostheses are generally constituted by a metal core (for example, a titanium alloy), an optional sheath of cladding around the core, and an outer cladding of textile for suturing. Rigid annuloplasty prostheses are described, for example, in U.S. Pat. No. 4,055,861 by Carpentier et al., issued Nov. 1, 1977, and U.S. Pat. No. 3,656,185 by Carpentier et al., issued Apr. 18, 1972.

Rigid prostheses, although satisfactory as far as reinstatement of the shape and dimensions of the valve annulus are concerned, do not allow the annulus of the valve to flex along the base of the posterior cuspid in such a way as to assist the cardiac muscle movements. Consequently, significant stress is imposed on the suture points subjected to torsion and traction, which prevents natural behavior of the valve.

Subsequently, semi-rigid or completely flexible prosthesis models were proposed. Completely flexible annuloplasty prostheses are described, for example, in U.S. Pat. No. 5,041,130 by Carpentier et al., issued Aug. 20, 1991, U.S. Pat. No. 5,716,397 by Myers et al., issued Feb. 10, 1998, U.S. Pat. No. 6,102,945 by Campbell et al., issued Aug. 15, 2000, and U.S. Pat. No. 5,064,431 by Gilbertson et al., issued Nov. 12, 1991. The completely flexible prostheses follow the movements of the annulus during the cardiac cycle in an optimal manner. However, they have the disadvantage of not allowing the shape to be reconstructed in an optimal manner.

Semi-rigid prostheses seek to unite the advantages of the rigid type with those of the completely flexible type while avoiding the disadvantages of each. Semi-rigid annuloplasty prostheses are described, for example, in U.S. Pat. Nos. 5,061,277 by Carpentier et al., issued Oct. 29, 1991, U.S. Pat. No. 5,104,407 by Lam et al., issued Apr. 14, 1992, U.S. Pat. No. 5,674,279 by Wright et al., issued Oct. 7, 1997, U.S. Pat. No. 5,824,066 by Gross et al., issued Oct. 20, 1998, U.S. Pat. No. 5,607,471 by Seguin et al., issued Mar. 4, 1997, and U.S. Pat. No. 6,143,024 by Campbell et al., issued Nov. 7, 2000.

In particular, U.S. Pat. No. 5,104,407 describes a ring prosthesis comprising an annular support element which is substantially more rigid in one part than in the remainder. This more rigid part projects transversely with respect to the general plane in which the remaining part of the support element lies. On the other hand, U.S. Pat. No. 5,607,471 describes a ring prosthesis having variable transverse sections, and therefore differentiated rigidity along its circumferential extent.

All these known prostheses have, however, limitations in relation to the possibility of exhibiting a variable rigidity in dependence on the point and/or direction and/or mode of application of the stresses. For example, U.S. Pat. No. 5,104,407 provides a structure with variable rigidity in the plane of the ring, but with a limited possibility of flexure outside this plane. On the other hand, U.S. Pat. No. 5,607,471 describes technical arrangements able to guarantee an improved flexibility out of the plane of the annulus. However, the possibility of effectively obtaining characteristics of variable rigidity of the prosthesis, for example, in its localised portions as well, appears significantly limited by the necessity to vary the area of the entire resistant section of the internal element. Moreover, the technical arrangements described in U.S. Pat. No. 5,607,471 do not allow an optimal behavior of the prosthesis in response to stresses in a tangential direction to be obtained (that is to say stresses directed along its longitudinal axis, which is usually closed in a ring), the rigidity in response to traction and compression at the same point of the internal element being substantially undifferentiated.

SUMMARY

The present invention provides a prosthesis for annuloplasty, the rigidity of which can be made variable in a desired manner in dependence on the point, direction and mode (traction, compression, flexion, torsion) of application of the stresses. According to the invention, this is achieved thanks to a prosthesis for annuloplasty comprising a laminar or tubular element having a plurality of apertures in at least one portion. This element can then be defined hereinafter in the present description as "perforated." In the perforated element, the apertures can be formed substantially according to any arrangement and with any shape and dimensions, so as to obtain the desired rigidity variation. For example, a prosthesis provided with such a perforated element can have markedly different rigidity whilst having a constant transverse section, so as to satisfy possible requirements of uniformity of dimensions.

The perforated element can be formed in its laminar form both with a flat development and with various three-dimensional shapes. Preferably, however, the perforated element is made in a tubular shape because this shape allows a more flexible and efficient arrangement of the apertures for the purpose of influencing the properties of rigidity of the prosthesis. As a matter of fact, the transverse section of the perforated tubular element can be of any shape. A circular transverse section is preferred for reasons of practicality and simplicity of production.

The prostheses of the invention have the additional advantage of an easier suturability since the apertures formed in the perforated element can constitute, if necessary, preferential transit ways for the passage of a suture needle.

There are no particular limitations in relation to the material usable for the production of the perforated element. The perforated element can be produced in metal, polymeric, or composite material. For their part, the apertures can be formed in the perforated element with any conventional technology. For example, if the perforated element is made of metal, the apertures can be formed by piercing a pre-formed tube by a laser, electroerosion, or cutting. If the perforated element were formed of polymeric material, it could be directly formed into its definitive shape by moulding technologies. Overall, therefore, the production of the prosthesis of the invention is simple and economical.

Further advantages and characteristics of the invention will become apparent from the following detailed description provided purely by way of non-limitative example, with reference to the attached drawings.

BRIEF DESCRIPTION OF THE DRAWINGS

FIG. 2 is a prospective view, on an enlarged scale, of a tubular element forming part of the prosthesis of FIG. 1.

FIGS. 3 to 6 are perspective views of respective alternative embodiments of the tubular element of FIG. 2.

FIG. 7 is a plan view, partially in section, of a further alternative open ring type (or "open loop type") embodiment of the prosthesis of the invention.

DETAILED DESCRIPTION

Figure 1:
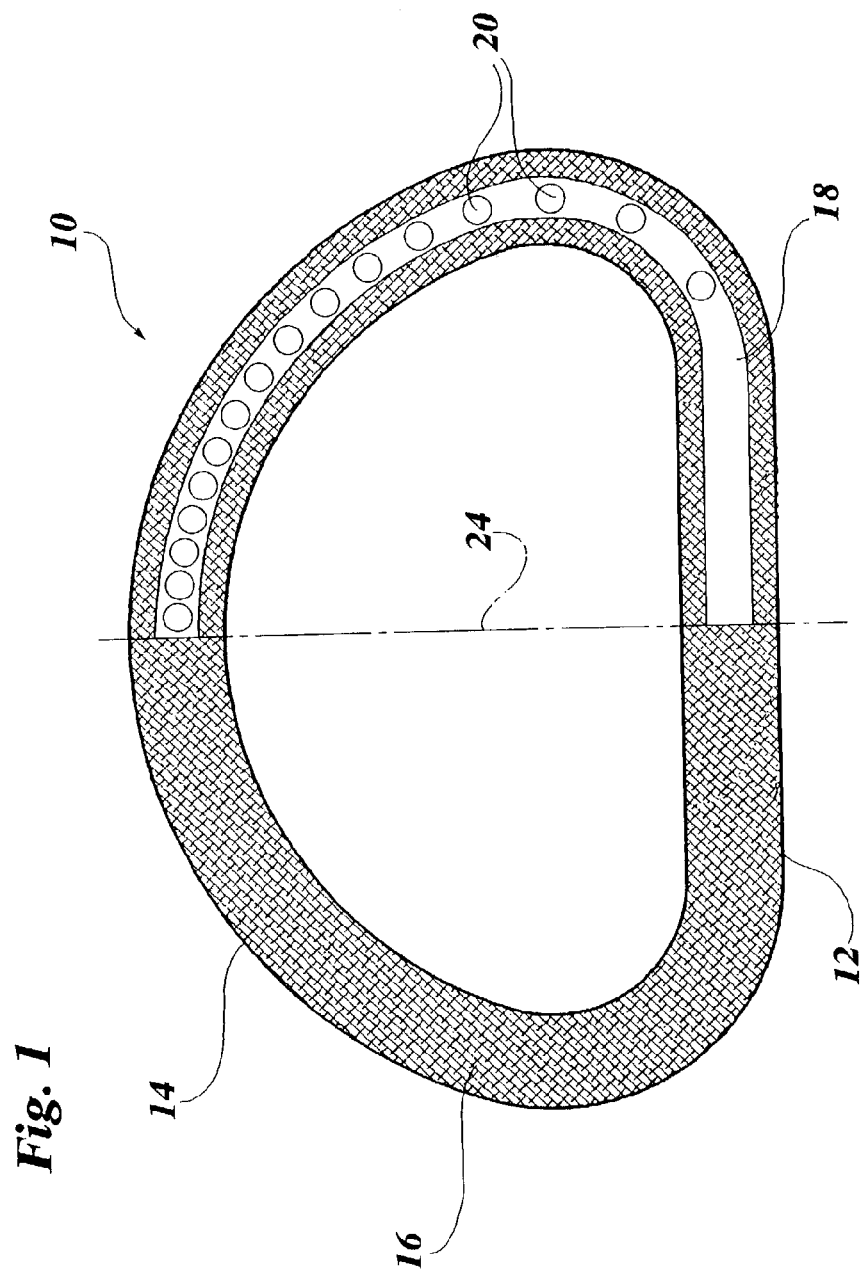
FIG. 1 is a plan view, partially in section, of a prosthesis of the invention of closed ring type (or "closed loop type").

The reference 10 indicates in FIG. 1 a prosthesis for annuloplasty. The shape of this prosthesis generally reproduces the geometry of the annulus of a mitral valve. This prosthesis has a closed ring shaped in the form of a D with an approximately rectilinear intertrigonal section 12 and a curved section 14. The prosthesis 10 is externally clad, in a manner known per se by a sheath 16 of biocompatible material. Preferably the sheath is made from materials chosen from the group consisting of polymers, synthetic textiles, biological tissues and their combinations. The sheath 16 covers a tubular ring element 18 having a transverse section of constant circular shape over its entire extent. The element 18 has in its wall (FIG. 2) a plurality of circular apertures 20 spaced along two lines parallel to the longitudinal axis 22 of the element 18 and diametrically opposite one another across the axis 22 in such a way that the apertures 20 have a spatial orientation substantially parallel to the general plane of the prosthesis 10. Preferably, there are no such apertures in the intertrigonal section 12, which must be more rigid, whilst they gradually become more closely spaced towards the central part of the curved section 14, which must be more flexible. The internal cavity of the element 18 may possibly be filled, partially or totally, with elastomeric material 23 in particular silicone, polyurethane and their mixtures, as for example described in U.S. patent Ser. No. 10/164,358, filed Jun. 5, 2002, the contents of which are hereby incorporated herein by reference.

The surface of the tubular element 18 and/or of the sheath 16 can be clad partially or totally with a thin layer of hemocompatible carbon, for example turbostratic carbon. The procedure for the production of such a cladding is, for example, described in the U.S. Pat. Nos. 5,084,151, 5,387,247, 5,370,684, 5,133,845, and 5,423,886, the contents of each of which are hereby incorporated herein by reference. This cladding contributes to an improved hemocompatibility of the prosthesis 10 and to a controlled tissue growth of the receiving organism.

FIG. 3 illustrates an alternative embodiment of the tubular element 18, which has, in addition to the apertures illustrated in the preceding FIG., further apertures 20 disposed along two lines parallel to the longitudinal axis 22 of the element 18 and diametrically opposite across the axis 18 so as to have a substantially transverse spatial orientation with respect to the general plane of the prosthesis 10. The presence of the apertures 20 in the arrangement just described influences the rigidity characteristics of the prosthesis 10 under the action of stresses which act both in the general plane and transversely with respect to it. In particular, the prosthesis can be rendered, for example, less rigid against stresses which act in its general plane along an antero-posterior direction (that is to say in a direction distinguished by the reference numeral 24 in FIG. 1), with respect to stresses which act in the general plane along a direction orthogonal to the antero-posterior direction. As far as the rigidity characteristics against stresses which act transversely with respect to the general plane of the prostheses 10 are concerned, they are for example chosen in such a way as to facilitate the assumption of a saddle shape in certain phases of the cardiac cycle.

The desired characteristics of variation in flexibility can also be obtained with a suitable variation of the dimensions of the apertures 20 of the element 18, as illustrated for example in FIG. 4.

FIG. 5 illustrates a further embodiment of the tubular element 18, in which the apertures 20 are formed in the shape of rings interrupted along a generatrix by a bridge 26 connecting adjacent portions 28, also of annular shape, of the tubular element 18. Such apertures 20 can be characterized by their extent (a) in the axial direction, the extent (b) in the axial direction of the tubular portions 28 interposed between two adjacent apertures 20, and the extent (c) of the bridges 26 in the circumferential direction. The values of (a), (b), and (c) can be selected independently at will and maintained constant or made to vary along the axial extent of the element 18 so as to determine the rigidity of the prosthesis 10 in a desired manner in dependence on the point and direction of application of the stresses.

FIG. 6 illustrates a further embodiment of the tubular element 18, in which the apertures 20 have a sinuous shape limited in one or more portions by edges 30 in contact, or almost in contact, in the absence of external stresses. A prosthesis provided with a perforated tubular element 18 of this type opposes enlargement of the apertures 20 with a predetermined force in response to a traction stress, allowing the prosthesis to extend in the axial direction, whilst further closure of the apertures 20 in response to a compression stress is in fact prevented by the contacting edges 30, so that the behavior of the prosthesis is similar in this case to that of a rigid body. Such a prosthesis thus has differentiated rigidity in response to stresses acting in the axial direction, being rather rigid in response to compression stresses but on the other hand deformable in response to traction stresses acting in the opposite sense along the same direction. Such behavior is particularly convenient for encouraging, on the one hand, the natural dilatation of the annulus in the diastolic phase and, on the other hand, to guarantee the absence of compression and corrugation phenomena (pleating) following surgical suture during a valve repair operation.

It goes without saying that the arrangements of the apertures 20 previously illustrated and/or described can be combined in any way in different portions of the same perforated element 18 so as to regulate the rigidity of the prosthesis 10 in a desired manner in dependence on the point and direction of application of the stresses. Equally it is also possible, in embodiments of the perforated element 18 not illustrated, to arrange the apertures in an irregular manner rather than in a regularly repeating pattern.

FIG. 7 illustrates a further embodiment of the prosthesis of the invention having an open ring shape and having a perforated element 18 of laminar or tubular structure. In this case, too, by varying the shape, dimensions and/or spacing of the apertures 20 it is possible to obtain the desired variations in rigidity.

Naturally, the principle of the invention remaining the same, the details of construction and the embodiments can be widely varied with respect to what has been described purely by way of example, without by this departing from its ambit.

What is claimed is:

1. An annuloplasty prosthesis for implantation in a cardiac valve annulus, the prosthesis comprising:
   a monolithic ring element having a longitudinal axis, a curved portion, and a generally straight portion, the curved portion having a first end region and a second end region, the generally straight portion extending between the first end region and the second end region; and
   a plurality of apertures disposed along substantially the entire curved portion, wherein the apertures are oriented generally transverse to the longitudinal axis, and further wherein at least one of a size, a shape, or a position of each aperture is selected such that the curved portion is more flexible than at least a portion of the straight portion.

2. The prosthesis of claim 1 wherein at least one of a size, a shape, or a position of each aperture is selected such that the ring element has a differentiated flexibility depending on the location and direction of application of an external stress.

3. The prosthesis of claim 1 wherein the curved portion has a center region and first and second end portions, and wherein at least one of a size, a shape, or a position of each aperture is selected such that the curved portion is more flexible near the center region than near the end portions.

4. The prosthesis of claim 1 wherein the ring element is covered by one or more biocompatible materials.

5. The prosthesis of claim 4 wherein the one or more biocompatible materials are chosen from the group consisting of polymers, synthetic textiles, and biological tissues.

6. The prosthesis of claim 4 wherein at least a portion of a surface of the one or more biocompatible materials is clad with hemocompatible carbon.

7. The prosthesis of claim 1 wherein the ring element has an internal cavity, and wherein the internal cavity is at least partially filled with an elastomeric material.

8. The prosthesis of claim 7 wherein the ring element is covered by a textile sheath.

9. The prosthesis of claim 8 wherein at least a portion of the sheath is clad with hemocompatible carbon.

10. An annuloplasty prosthesis comprising:
    a monolithic ring element having a size and a shape generally corresponding to a cardiac valve annulus and including a longitudinal axis, a first portion having first and second end regions, and a second portion extending between the first end region and the second end region; and
    a plurality of apertures disposed along substantially the entire first and second portions, wherein the apertures are configured or disposed in such a way that the first portion is more flexible than the second portion, and further wherein at least some of the apertures are oriented generally transverse to the longitudinal axis.

11. The prosthesis of claim 10 wherein the apertures are configured or disposed in such a way that the ring element has a differentiated flexibility depending on the location and direction of application of an external stress.

12. The prosthesis of claim 10 wherein the ring element is covered by one or more biocompatible materials.

13. The prosthesis of claim 12 wherein the one or more biocompatible materials are chosen from the group consisting of polymers, synthetic textiles, and biological tissues.

14. The prosthesis of claim 12 wherein at least a portion of a surface of the one or more biocompatible materials is clad with hemocompatible carbon.

15. The prosthesis of claim 10 wherein the ring element has an internal cavity, and wherein the internal cavity is at least partially filled with an elastomeric material.

16. The prosthesis of claim 15 wherein the ring element is covered by a textile sheath.

17. The prosthesis of claim 16 wherein at least a portion of a sheath is clad with hemocompatible carbon.

18. An annuloplasty prosthesis comprising:
    a monolithic ring element configured for implantation in a cardiac valve annulus and having a longitudinal axis, a first portion having first and second end regions, and a second portion extending between the first end region and the second end region; and
    a plurality of apertures disposed along substantially the entire first portion, wherein each aperture is oriented generally transverse to the longitudinal axis and sized, shaped, or positioned along at least the first portion such that the first portion is more flexible than at least a part of the second portion.

19. The prosthesis of claim 18 wherein at least two of a size, a shape, or a position of each aperture are selected such that the first portion is more flexible than at least a part of the second portion.

20. The prosthesis of claim 18 wherein each aperture is sized, shaped, or positioned such that the ring element has a differentiated flexibility depending on the location and direction of application of an external stress.

21. The prosthesis of claim 18 wherein the prosthesis is generally planar, and wherein each aperture is sized, shaped, or positioned such that the ring element has a first flexibility in response to a first external stress acting in the general plane of the prosthesis and a second flexibility in response to a second external stress acting generally transverse to the general plane of the prosthesis.

22. The prosthesis of claim 18 wherein the ring element is covered by one or more biocompatible materials selected from the group consisting of polymers, synthetic textiles, and biological tissues.

23. The prosthesis of claim 22 wherein at least a portion of a surface of the one or more biocompatible materials is clad with hemocompatible carbon.

24. The prosthesis of claim 18 wherein the ring element has an internal cavity, and wherein the internal cavity is at least partially filled with an elastomeric material.

25. The prosthesis of claim 24 wherein the ring element is covered by a textile sheath.

26. The prosthesis of claim 25 wherein at least a portion of a sheath is clad with hemocompatible carbon.

* * * * *